United States Patent [19]

Gaudreault et al.

[11] Patent Number: 5,300,104
[45] Date of Patent: Apr. 5, 1994

US005300104A

[54] THERMOTHERAPEUTIC PAD

[76] Inventors: Yvon Gaudreault, 58 des Pins, St-Charles Borromée, Joliette (Québec), Canada, J6E 1X7; Monique Lebeau, 30, rue Ste-Adèle, St-Charles Borromée (Québec), Canada, J6E 1K5; Rita Robitaille, 79, des Ormeaux, app 1, St-Charles Borromée, (Québec), Canada, J6E 7J8

[21] Appl. No.: 9,028

[22] Filed: Jan. 26, 1993

[30] Foreign Application Priority Data

Oct. 20, 1992 [GB] United Kingdom ............... 9222037

[51] Int. Cl.⁵ .................................................. A61F 7/00
[52] U.S. Cl. ....................................... 607/114; 426/113
[58] Field of Search ............... 128/399, 402, 403, 379, 128/380; 426/113; 62/530; 206/0.5; 604/368, 291

[56] References Cited

U.S. PATENT DOCUMENTS

| | | | |
|---|---|---|---|
| 3,888,256 | 6/1975 | Studinger | 604/368 |
| 3,900,035 | 8/1975 | Welch | 128/403 |
| 4,045,387 | 8/1977 | Fanta et al. | 604/368 |
| 4,514,426 | 4/1985 | Jordan et al. | 428/113 |
| 4,659,495 | 4/1987 | Figliola | 206/0.5 |
| 4,865,012 | 9/1989 | Kelley | 128/403 |

Primary Examiner—Mark S. Graham
Attorney, Agent, or Firm—Pierre Lespérance; Francois Martineau

[57] ABSTRACT

A flexible heat pad for heat transfer to a person's limb. The pad consists of a fabric (preferably cotton) envelope enclosing a load of cereal grains, preferably oats. Preferably, the water content of the oat is precisely monitored to remain within the 9 to 14% range by weight of the oat total weight. The quantity of oat grains inside the cotton envelope must be such as to provide even oat distribution within the cotton envelope enclosure, after deformation, whereby localized grainless pockets within the pad enclosure are substantially prevented. The pad is pre-heated for about two minutes inside a micro-wave oven, at full power setting, before use. Thermal inertia of the oat thereafter allows continuous heat diffusion to the limb for about half an hour. The pad may alternately be put into the freezer for at least four to six hours, to thereafter diffuse cold to the swollen limb part of a mammal.

4 Claims, No Drawings

THERMOTHERAPEUTIC PAD

FIELD OF THE INVENTION

This invention relates to flexible pad devices that continuously release stored heat or cold, for a set duration, onto a mammal (human or animal) body limb.

BACKGROUND OF THE INVENTION

Known therapeutic heat transfer devices relieve aches, pains, tensions in mammals (warm-blooded creatures, such as humans), and reduce swelling, among other things; they also have cosmetic use for opening the pores of the skin, as in beauty treatments and dermatological uses. This is achieved by promoting blood circulation through the limbs against which the heat transfer device is applied.

The effects of localized thermal transfer to bodily parts with these known thermal transfer devices is well documented in the art. Such heat transfer devices include:

(a) the simple hot water-filled bag, or conversely, the ice pack filled with water ice;

(b) electric blankets, which include insulated, multilayered, flexible sheets, and a heat cell embedded within the sheets and generating continuous heat upon plugging the electric wire thereof in an electrical wall plug;

(c) chemical steam packs, which generate heat upon unsealing the pack, thus enabling exothermic oxydation of the air-responsive, reactive chemical agent within the pack, for a period of about half an hour—they are used e.g. by alpine skiers inside their hand gloves; see for example U.S. Pat. No. 3,874,504 to Verakas;

(d) mineral-filled heat pads, with a flexible envelope enclosing granular mineral material (usually sand or vulcanite); the pad is pre-heated in an oven before use, to enable slow diffusion of heat absorbed by the mineral crystals—see for example international patent application No PCT/EP90/00785 published on Nov. 29, 1990 in the name of Herbert Hans WAGNER;

(e) gel-based thermal packs, with an envelope enclosing a gel-state material having a substantial water content associated with a liquid-absorbing core, this core including for example propylene glycol and formaldehyde (to extend the overall thermal range of the gel-state of the material before reaching freezing or boiling state)—see for example U.S. Pat. Nos. 4,488,552 issued Dec. 18, 1984 to Micropak manufacturing, inc., and 4,920,964 issued May 1, 1990 to Jack Frost Laboratories inc.; these thermal packs release stored heat slowly, after being pre-heated for a while in an oven, as with the mineral-filled heat pads, supra.

These prior art heat transfer devices, although effective, have a number of drawbacks. The electric blankets, for one, generate magnetic fields. Currently, there is considerable controversy as to whether or not long exposure of biological tissues to high levels of electromagnetic fields is linked to cancerous cell development. Extensive studies on the interaction of electric fields with living matter have brought concerns to the scientific community as to the health hazards associated with electric blankets. See for example the "CRC Handbook of biological effects of electromagnetic fields", Charles POLK editor, CRC Press, Boca Raton Fla. [1986].

Chemical steam packs are of the disposable type, i.e. they can be used only once. Their cost is accordingly high, relative to reusable heat transfer pads such as the mineral-filled pads and the gel pads. Moreover, the dosage of reactive agent inside the sealed pouch is critical in order not to overheat the pouch—indeed, some cases of bodily injuries have been reported a few years ago in the press, from skin exposure to such chemical steam packs due probably to an improperly measured amount (i.e. an amount greater than required) of reactive chemical agent in the pouch.

Gel type heat pads have a tendency to burst if the preheating period exceeds the recommended time period. The margin for error is very small, as is indeed candidly reported in the specification of the two above-noted gel-type U.S. patents. A burst pad becomes unreusable, and may further constitute a safety hazard. Moreover, gel pads tend to produce a so-called "moist" heat, which may not be desirable for everybody.

Mineral-based heat transfer pads have other drawbacks. Because of the extremely low water content of the granular mineral occur between the mineral granules as the flexible pad is repeatedly bent to fit around the various limb parts. Eventually, these granules accordingly become powdery (i.e., their granulometry progressively decreases), so that they may come to escape from the pad through the porous envelope wall. Moreover, mineral materials such as sand define granules each having relatively sharp external edges; such sharp edges are certainly uncomfortable to the skin as they indirectly come in contact therewith through the pad envelope wall. Also, because the granulometry of sand is quite small, it has been found by the three present joint inventors that the granular material pressure load-induced movement within the pad envelope and consequent distributive flow therein tend to easily generate empty grainless pockets within the pad envelope. In other words, instead of the granular material desirably spreading equally all along the enclosure of the pad envelope, the sand will tend to gather at the two opposite ends of the pad, under gravity-borne forces, while the intermediate section thereof (that is, the main pad section coming in contact with the body part to be soothed) will be substantially free from any heat-releasing core material (the two corresponding sections of the opposite main walls of the envelope will abut flatly against one another), an inefficiency.

OBJECTS OF THE INVENTION

The gist of the invention is therefore to provide a thermal-transfer device, that will attempt to overcome the drawbacks outlined in the preceeding background of the invention paragraph.

More specifically, an important object of the invention is to provide a heat- or cold-transfer pad, made solely from purely "natural" components.

Another important object of the invention is that the heat transfer pad includes granular material of such granulometry, water content and pouch loading volume, that well distributed flow of the granular material (i.e., good shape retention) inside the pad envelope is consistently achieved after each bending action on the pad, without the formation of substantial empty grainless pockets therewithin.

A general object of the invention is to provide such a heat-transfer device, of inexpensive make, of reusable nature, of safe handling, and of quick and simple method of use.

Other objects of the invention include: that the pad be resistant to heat-induced bursting; that the pad envelope be made from a thermally insulated material whereby direct, health-safe application of the pad on the skin is enabled; and that the present thermotherapeutic pad be both of high thermal inertia and high moisture inertia.

SUMMARY OF THE INVENTION

Accordingly with the objects of the invention, there is disclosed a thermotherapeutic pad for use in soothing mammal body limbs, comprising an envelope, made from a flexible, smooth, porous, thermally conductive sheet material, and a granular material, enclosed within said envelope; wherein said granular material consists of grains of cereals, said grains of cereal being characterized by a high moisture inertia as well as by a high thermal inertia.

Preferably, said grains of cereals have a water content set to range between approximately 9 and 14% by weight of the cereal grains. Profitably, said cereal grain water content ranges more particularly between 10 and 11% by weight; advantageously, said grain cereal is oat; most preferably, said oat grain water content has a substantially constant value of approximately 10.5% by weight.

Profitably, said envelope sheet material is cotton, the cotton sheet defining a peripheral stitch line circumscribing the enclosure defined by said envelope. Preferably then, said cotton enclosure, wherein the envelope enclosure defines a smooth continuous inner surface whereby free distributive grain flow within the pad envelope is not hampered during pad flexing. Most preferably, all of said oat grains define a substantially constant, set granulometry, said grain granulometry being specifically selected to enable free distributive flow of grains within said pad envelope during repeated pad flexing, while positively preventing the formation of grainless pockets inside the pad envelope enclosure, at the elbowed portions of the flexed thermal pad.

The invention also concerns a method of use of a flexible thermotherapeutic pad, said pad of the type including a cotton-like envelope and a cereal grain material enclosed within said envelope, said method including the following steps: (a) submitting said pad to a thermal stress selected from the group comprising: heating the pad inside a micro-wave oven for a period of time sufficient to enable non-burning heat diffusion, heating the pad inside a convection oven with the pad covered with an aluminum protective sheet for the same corresponding duration, or freezing the pad inside a freezer for a duration sufficient to enable the pad to diffuse non-burning cold for an appreciable time; (b) applying the pad against a body limb part to be soothed; (c) flexing the pad arcuately around said body limb part, whereby free distributive flow of said cereal grains occur within said pad envelope without substantial grainless pocket formation therewithin.

DETAILED DESCRIPTION OF THE INVENTION

The flexible heat pad for heat transfer to a person's limb consists of a fabric envelope enclosing a load of cereal grains, preferably oats. The water content of the oat is preferably precisely monitored to remain between 9 and 14% by weight of the oat total weight. The quantity of oat grains inside the cotton envelope, and the oat grain granulometry, are carefully selected in such a way as to provide even oat distributive flow within the cotton envelope enclosure, after deformation, whereby localized grainless pocket are substantially prevented. In one embodiment, a pad with a one kilogram oat filler load is to be preheated for one to two minutes inside a micro-wave oven, before use. Thermal inertia of the oat allows heat diffusion for about half an hour. That same pad may alternately be put in the freezer for four to six hours, to thereafter diffuse stored cold to a swollen limb part.

The oat used in the pad is pre-prepared as follows. First, oat is stored inside a conventional grain elevator, where approximately 13 to 16% by weight. At this water content ratio, moisture inertia is relatively small, i.e. that the oat grains will quickly respond to a variation in water content upon variation of the ambient air humidity level. The oat grains are then trimmed, to eradicate biological contaminants, and screened, to remove inorganic contaminants, whereby the oat grains will be able to maintain their natural features for a long period of time. The oat grains are then dryed inside a drying tank, with propane gas, so as to lower their water content to at least 13 or 14% by weight; preferably, there is further dry-heating, to bring down still further the water content, down to 12, more preferably 11, and down to about 9% by weight, although the ideal setting has been found to be of about 10,5% of water content. This can take a number of days of constant heat-drying.

Below 10,5% by weight of oat water content, the thermal pad becomes hot very rapidly, a concern for burning the skin. Below 9% by weight of water content, the cost for further drying of the oat becomes prohibitive, and moreover, granular grinding (and associated problems as outlined in the Background of the invention paragraph) becomes a concern.

It has been discovered by the present joint inventors that unexpected high performance in the heat transfer features of the present thermal pad was achieved, where oat water content was set at the selected range from 10.5 to 11%. This unexpected performance is linked to the important jump i.e. increase in moisture inertia levels, gained as the oat water content decreases, starting from approximately 14 or 13.5, down to the spectacularly high moisture level inertia value reached at the 10,5 to 11% range. With such high inertia values, even if ambient air humidity level is relatively high, the oat grain will be extremely resistant to change (i.e. to increase) in their water content; indeed, it will take several days for the oat grain at a 10,5% water content to only slightly increase their water content, even in a very moist air environment.

Of course, the oat pad will have to be stored in a dry long-term the low water content of the oat grains.

As the water content decreases still further below the 10.5% mark, problems gather: the drying costs become progressively higher and higher, some grinding action of the granular material occurs thus altering the carefully adjusted granulometry of the cereal grains, whereby the various problems outlined in the Background of the invention paragraph (supra) accumulate. The present joint inventors have determined that below 9% of water content or so for the grain oats, the efficiency of manufacturing operations was substantially decreasing.

For the constituting material of the present thermal pad porous, and is very smooth and thus comfortable to the skin. (This is why it is the preferred material for baby's diapers). The cotton envelope wall should be relatively thick—although not too thick, otherwise a water barrier would undesirably be established (the oat grains must be allowed to "breath"). One example of a functional thermal pad according to the invention includes a cotton envelope having a density of about 6 ounces per square yard, the cotton envelope enclosing a load of approximately one kilogram of cereal (preferably oat) grains. The cotton envelope is made from a single cotton sheet, bent in two and stitched at its peripheral edge. The stitch lines are most preferably oriented to the outside of the present thermal pad, so as not to hamper in any way the free, smooth, distributive flow of granular oat material, this distributive grain flow being responsive to the repeated flexing of the thermal pad around the limb parts to be soothed.

Acceptable envelope materials other than cotton would include flannel, GORTEX (a trademark) (a sheet material which allows one-way breathing i.e. from the inside to the outside of the pad only, linen, or the like fabric materials, provided these material can withstand a micro-wave radiative environment. The envelope material should be a material which will thermally insulate the body part skin surface from the high thermal inertia inner pad cereal grain filling, to prevent any "burning" sensation at the time of contact; specifically undesirable surface materials in this respect are metallic surfaces and the like materials having low specific heat ratios.

Oat grains are preferred, because each grain has a smooth, generally ovoidal surface that will be most comfortable to the skin, as the grain-filled pad is rolled over and maintained in contact with the limb to be soothed. Oat grain are further almost odorless, when heated. The type of cereals envisioned, other than the preferred oats, include: barley, wheat, buckwheat, rice and corn. However, compared to oat grains:

(a) corn undesirably releases noticeable odours, when heated (yet has the advantage of being particularly lightweight compared to the other grain cereals);
(b) wheat grains are undesirably rough-surfaced, or knurled; and
(c) buckwheat grains undesirably have some sharp edges.

The loading volume of oat grains inside the cotton the flexibility of the pad. A too small volume brings about grainless pockets inside the pad, which therefore reduce the efficiency of the thermal transfer properties of the present thermal pad.

The present thermal pad preferred method of preheating the one kg load of oat grains in the thermal pad (the corresponding 6-ounce per square yard cotton envelope is "micro-wave transparent") is through a micro-wave oven (at maximum setting, for one to two minutes). However, conventional convection-type ovens are not excluded; but then, the cotton pad should be surrounded with an aluminum sheath, to prevent alteration of the cotton during heating.

The thermal pad could alternately have various shapes, including the shape of a slipper, of a shirt or trouser, or of any garment or indeed any type of padded furniture or padded structure. Race horses may have the articulation of their legs soothed (in case of swelling inflammation) by leg pads surrounding the leg section, these leg pad being filled with oat grains according to the present invention, these oat pads being pre-chilled inside the freezer for a number of hours. The pad could also have the shape of a wine-bottle receiving pouch, for cooling white wine before serving. Or, for example, still another embodiment would include a cotton pad divided into a number of separate pockets or "cells", each cell being separated from the adjacent cells by stitch lines; each cell includes a cereal grain filling not in communication with that of the other cells; such a pad would be particularly advantageous for body regions having right-angle portions, e.g. shoulder areas, so that the pad could intimately follow the body contours.

In any of these embodiments, the thermal transfer features remain the same, namely: upon freezing the oat grains, there is soothing of bursitis, migraines, ankle twist, body fever, tendinitis; and upon heating the oat grains, there is soothing of muscular pains, belly aches, arthritis, arthrosis, neck stiffness, tendinitis, bursitis, or for simply relaxing.

The present thermal pad must remain dry at all times (it will loose its advantageous features if soaked in water for some period of time).

It is understood that cereal grains have a natural moisture content which is very low.

I claim:

1. A thermotherapeutic pad for use in soothing mammal body limbs, comprising an envelope, made from a flexible, smooth, porous, thermally conductive sheet material, and a granular material exclusively of any free liquid, said granular material being enclosed within and retained by said envelope; wherein said granular material consists of grains of cereals, said grains of cereal being unsaturated and unbound to one another and having a water content ranging between 10 and 11% by weight of the cereal grains, said grain cereal being oat; whereby free distributive flow thereof within said envelope during pad flexing conformingly against a body limb is enabled, said grains of cereal being characterized by a high moisture inertia as well as by a high thermal inertia; wherein said envelope sheet material is cotton, the cotton sheet defining a peripheral stitch line circumscribing the enclosure defined by said envelope.

2. A thermotherapeutic pad as defined in claim 1, wherein said cotton sheet stitch line is oriented outwardly from said envelope enclosure, wherein said envelope enclosure defines a smooth inner surface whereby free distributive grain flow within the pad envelope is not hampered during pad flexing.

3. A thermotherapeutic pad as defined in claim 2, wherein all of said oat grains define a substantially constant, set granulometry, said grain granulometry being specifically selected to enable free distributive flow of grains within said pad envelope during repeated pad flexing, while positively preventing the formation of grainless pockets inside the pad envelope enclosure, at the elbowed portions of the flexed thermal pad; said grain granulometry remaining substantially constant throughout use, even after repeated pad flexings.

4. A method of use of a flexible thermotherapeutic pad, said pad including a cotton-like envelope and a cereal grain material exclusively of any free liquid enclosed within and retained by said envelope, said cereal grain material being unsaturated and unbound to one another whereby free distributive flow thereof within said envelope during pad flexing is enabled, said grains of cereal being of the type having high thermal inertia as well as high moisture inertia, and the granulometry of said granular material remaining substantially constant even after repeated pad flexing, said method including the following steps:

(a) submitting said pad to a thermal stress selected from the group comprising: heating the pad inside a micro-wave oven for a period of time sufficient to enable the cereal grains to reach a high temperature short of a skin-burning temperature, heating the pad inside a convection oven with the pad covered with an aluminum protective sheet for a corresponding time period, or freezing the pad inside a freezer for a period of time sufficient to enable the grain cereals to reach a subfreezing temperature short of a skin-burning temperature;

(b) applying the pad against a mammal limb part to be soothed;

(c) flexing the pad arcuately around said body limb part, whereby free distributive flow of said cereal grains occur within said pad envelope without substantial grainless pocket formation therewithin.

* * * * *